(12) United States Patent
Djupesland et al.

(10) Patent No.: US 10,722,667 B2
(45) Date of Patent: Jul. 28, 2020

(54) NASAL ADMINISTRATION

(71) Applicant: OptiNose AS, Oslo (NO)

(72) Inventors: Per Gisle Djupesland, Oslo (NO); Roderick Peter Hafner, Swindon (GB)

(73) Assignee: OptiNose AS, Oslo (NO)

( * ) Notice: Subject to any disclaimer, the term of this patent is extended or adjusted under 35 U.S.C. 154(b) by 267 days.

(21) Appl. No.: 15/481,975

(22) Filed: Apr. 7, 2017

(65) Prior Publication Data

US 2017/0274164 A1  Sep. 28, 2017

Related U.S. Application Data

(63) Continuation of application No. 12/594,365, filed as application No. PCT/GB2008/001226 on Apr. 7, 2008, now Pat. No. 9,649,456.

(30) Foreign Application Priority Data

Apr. 5, 2007  (GB) .................................. 0706744.0

(51) Int. Cl.
*A61M 15/08* (2006.01)
*A61M 15/00* (2006.01)
(Continued)

(52) U.S. Cl.
CPC ......... *A61M 15/08* (2013.01); *A61K 31/4045* (2013.01); *A61M 15/003* (2014.02);
(Continued)

(58) Field of Classification Search
CPC ................ A61M 15/00; A61M 15/003; A61M 15/0035; A61M 15/0041; A61M 15/0098;
(Continued)

(56) References Cited

U.S. PATENT DOCUMENTS

| 605,436 A | 6/1898 | Kellogg |
| 642,748 A | 2/1900 | Manners |

(Continued)

FOREIGN PATENT DOCUMENTS

| EP | 0490689 | 6/1992 | | |
| EP | 0490689 A1 * | 6/1992 | ........... | C07D 209/16 |

(Continued)

OTHER PUBLICATIONS

Einer-Jensen et al., *Intranasal Absorption of Sumatriptan and Naratriptan: No Evidence of Local Transfer from the Nasal Cavities to the Brain Arterial Blood in Male Rats*, 22 Biopharm, Drug Dispos. 213-219 (2001).

(Continued)

*Primary Examiner* — Valerie L Woodward
(74) *Attorney, Agent, or Firm* — Servilla Whitney LLC

(57) ABSTRACT

A delivery device for and method of delivering a powdered substance, in particular a triptan, such as sumatriptan, to the posterior region of a nasal cavity of a subject, in particular for the treatment of headaches, for example, cluster headaches and migraine, and neuropathic pain, the delivery device comprising: a nosepiece for insertion into a nasal cavity of a subject through which the powdered substance is delivered to the posterior region of the nasal cavity of the subject, in particular the upper posterior two thirds of the nasal cavity; and a substance supply unit which is operable to deliver the powdered substance through the nosepiece.

17 Claims, 5 Drawing Sheets

(51) Int. Cl.
*A61K 31/4045* (2006.01)
*A61M 16/10* (2006.01)
*A61M 16/08* (2006.01)

(52) U.S. Cl.
CPC .... *A61M 15/0005* (2014.02); *A61M 15/0008* (2014.02); *A61M 15/0021* (2014.02); *A61M 15/0028* (2013.01); *A61M 15/0035* (2014.02); *A61M 15/0041* (2014.02); *A61M 15/0098* (2014.02); *A61M 16/0808* (2013.01); *A61M 16/1045* (2013.01); *A61M 16/1055* (2013.01); *A61M 16/1065* (2014.02); *A61M 2202/064* (2013.01); *A61M 2205/3606* (2013.01); *A61M 2210/0618* (2013.01); *A61M 2210/0625* (2013.01)

(58) Field of Classification Search
CPC .............. A61M 15/08; A61M 15/0005; A61M 15/0008; A61M 15/0021; A61M 15/0028
See application file for complete search history.

(56) References Cited

U.S. PATENT DOCUMENTS

| | | |
|---|---|---|
| 658,436 A | 9/1900 | Groth |
| 746,749 A | 12/1903 | Seidel |
| 794,641 A | 7/1905 | Ramey |
| 902,832 A | 11/1908 | Philbrook |
| 1,375,325 A | 4/1921 | Schaefer |
| 3,906,950 A | 9/1975 | Cocozza |
| 5,046,493 A | 9/1991 | Kropkowski et al. |
| 5,373,841 A | 12/1994 | Kyllonen et al. |
| 5,797,392 A | 8/1998 | Keldmann et al. |
| 6,019,100 A | 2/2000 | Alving et al. |
| 6,186,141 B1 | 2/2001 | Pike et al. |
| 6,240,918 B1 | 6/2001 | Ambrosio et al. |
| 6,648,848 B1 | 11/2003 | Keldmann et al. |
| 6,715,485 B1 | 4/2004 | Djupesland |
| D530,815 S | 10/2006 | Murphy et al. |
| 7,189,753 B1 | 3/2007 | Cady |
| 7,347,201 B2 | 3/2008 | Djupesland |
| 7,377,901 B2 | 5/2008 | Djupesland et al. |
| 7,481,218 B2 | 1/2009 | Djupesland |
| 7,543,581 B2 | 6/2009 | Djupesland |
| 7,700,125 B2 | 4/2010 | Reiner et al. |
| 7,740,014 B2 | 6/2010 | Djupesland |
| 7,784,460 B2 | 8/2010 | Djupesland et al. |
| 7,841,337 B2 | 11/2010 | Djupesland |
| 7,854,227 B2 | 12/2010 | Djupesland |
| 7,934,503 B2 | 5/2011 | Djupesland et al. |
| 7,975,690 B2 | 7/2011 | Djupesland |
| 8,047,202 B2 | 11/2011 | Djupesland |
| 8,146,589 B2 | 4/2012 | Djupesland |
| 8,171,929 B2 | 5/2012 | Djupesland et al. |
| 8,327,844 B2 | 12/2012 | Djupesland |
| 8,511,303 B2 | 8/2013 | Djupesland |
| 8,522,778 B2 | 9/2013 | Djupesland |
| 8,550,073 B2 | 10/2013 | Djupesland |
| 8,555,877 B2 | 10/2013 | Djupesland |
| 8,555,878 B2 | 10/2013 | Djupesland |
| 8,590,530 B2 | 11/2013 | Djupesland et al. |
| 8,596,278 B2 | 12/2013 | Djupesland |
| 8,800,555 B2 | 8/2014 | Djupesland |
| 8,875,704 B2 | 11/2014 | Djupesland et al. |
| 8,899,229 B2 | 12/2014 | Djupesland et al. |
| 8,910,629 B2 | 12/2014 | Djupesland et al. |
| D723,156 S | 2/2015 | Djupesland et al. |
| D725,769 S | 3/2015 | Djupesland et al. |
| 8,978,647 B2 | 3/2015 | Djupesland et al. |
| 9,010,325 B2 | 4/2015 | Djupesland et al. |
| 9,038,630 B2 | 5/2015 | Djupesland et al. |
| 9,067,034 B2 | 6/2015 | Djupesland et al. |
| 9,072,857 B2 | 7/2015 | Djupesland |
| 9,108,015 B2 | 8/2015 | Djupesland |
| 9,119,932 B2 | 9/2015 | Djupesland |
| 9,132,249 B2 | 9/2015 | Djupesland |
| 9,144,652 B2 | 9/2015 | Djupesland et al. |
| 9,168,341 B2 | 10/2015 | Djupesland |
| 9,205,208 B2 | 12/2015 | Djupesland |
| 9,205,209 B2 | 12/2015 | Djupesland |
| 9,272,104 B2 | 3/2016 | Djupesland |
| D759,805 S | 6/2016 | Djupesland |
| D761,951 S | 7/2016 | Djupesland |
| 9,452,272 B2 | 9/2016 | Djupesland et al. |
| 9,468,727 B2 | 10/2016 | Djupesland |
| D773,644 S | 12/2016 | Djupesland |
| 9,522,243 B2 | 12/2016 | Djupesland |
| 9,566,402 B2 | 2/2017 | Djupesland |
| 9,649,456 B2 | 5/2017 | Djupesland et al. |
| 2002/0117170 A1 | 8/2002 | Platz et al. |
| 2002/0158150 A1 | 10/2002 | Matsugi et al. |
| 2002/0177562 A1 | 11/2002 | Weickert et al. |
| 2003/0015190 A1* | 1/2003 | Rabinowitz ............ A61K 9/007 128/200.14 |
| 2003/0133877 A1 | 7/2003 | Levin |
| 2003/0183223 A1 | 10/2003 | Hailey et al. |
| 2004/0024330 A1 | 2/2004 | Djupesland et al. |
| 2004/0042972 A1* | 3/2004 | Truong-Le ........... A61K 9/0043 424/46 |
| 2004/0112378 A1 | 6/2004 | Djupesland |
| 2004/0112379 A1 | 6/2004 | Djupesland |
| 2004/0112380 A1 | 6/2004 | Djupesland |
| 2004/0138618 A1 | 7/2004 | Mazzoni |
| 2004/0149289 A1 | 8/2004 | Djupesland |
| 2004/0153033 A1 | 8/2004 | Mazzoni |
| 2004/0167158 A1 | 8/2004 | Edwards et al. |
| 2004/0182388 A1 | 9/2004 | Djupesland |
| 2005/0028812 A1* | 2/2005 | Djupesland ....... A61M 15/0091 128/200.21 |
| 2005/0034723 A1 | 2/2005 | Bennett et al. |
| 2005/0072430 A1* | 4/2005 | Djupesland ........ A61M 15/0091 128/206.11 |
| 2005/0126569 A1 | 6/2005 | Crowder et al. |
| 2005/0235992 A1 | 10/2005 | Djupesland |
| 2006/0096589 A1 | 5/2006 | Djupesland |
| 2006/0106227 A1 | 5/2006 | Reddy et al. |
| 2006/0107957 A1 | 5/2006 | Djupesland |
| 2006/0147389 A1 | 7/2006 | Staniforth et al. |
| 2006/0169278 A1 | 8/2006 | Djupesland et al. |
| 2006/0207596 A1 | 9/2006 | Lane |
| 2006/0219240 A1 | 10/2006 | Djupesland |
| 2006/0219241 A1 | 10/2006 | Djupesland |
| 2006/0225732 A1 | 10/2006 | Djupesland |
| 2006/0231094 A1 | 10/2006 | Djupesland |
| 2006/0289007 A1* | 12/2006 | Williams .......... A61M 15/0091 128/203.15 |
| 2007/0031340 A1 | 2/2007 | Hale et al. |
| 2007/0039614 A1 | 2/2007 | Djupesland |
| 2007/0053972 A1 | 3/2007 | Sakanishi et al. |
| 2007/0056586 A1 | 3/2007 | Price et al. |
| 2007/0125371 A1 | 6/2007 | Djupesland |
| 2007/0129665 A1 | 6/2007 | Dickens et al. |
| 2007/0175472 A1 | 8/2007 | Pipkin et al. |
| 2007/0186927 A1 | 8/2007 | Djupesland et al. |
| 2008/0161771 A1 | 7/2008 | Djupesland |
| 2008/0163874 A1 | 7/2008 | Djupesland |
| 2008/0221471 A1 | 9/2008 | Djupesland et al. |
| 2008/0223363 A1 | 9/2008 | Djupesland |
| 2008/0226736 A1 | 9/2008 | Caponetti et al. |
| 2008/0260848 A1 | 10/2008 | Nagata et al. |
| 2008/0289629 A1 | 11/2008 | Djupesland et al. |
| 2009/0101146 A1 | 4/2009 | Djupesland |
| 2009/0293873 A1 | 12/2009 | Djupesland et al. |
| 2009/0297457 A1 | 12/2009 | Bovet et al. |
| 2009/0304802 A1 | 12/2009 | Djupesland et al. |
| 2009/0314293 A1 | 12/2009 | Djupesland |
| 2009/0320832 A1 | 12/2009 | Djupesland |
| 2010/0035805 A1 | 2/2010 | Hafner |
| 2010/0051022 A1 | 3/2010 | Djupesland et al. |
| 2010/0057047 A1 | 3/2010 | Djupesland et al. |
| 2010/0199984 A1* | 8/2010 | Williams, III .... A61M 15/0065 128/200.23 |
| 2010/0242959 A1 | 9/2010 | Djupesland et al. |
| 2010/0282246 A1 | 11/2010 | Djupesland et al. |

(56) References Cited

U.S. PATENT DOCUMENTS

| | | |
|---|---|---|
| 2010/0288275 A1 | 11/2010 | Djupesland et al. |
| 2010/0300439 A1 | 12/2010 | Djupesland et al. |
| 2011/0023869 A1 | 2/2011 | Djupesland |
| 2011/0053827 A1 | 3/2011 | Hafner |
| 2011/0088690 A1 | 4/2011 | Djupesland et al. |
| 2011/0088691 A1 | 4/2011 | Djupesland |
| 2011/0114087 A1 | 5/2011 | Djupesland et al. |
| 2011/0126830 A1 | 6/2011 | Djupesland et al. |
| 2011/0259329 A1 | 10/2011 | Djupesland et al. |
| 2011/0318345 A1 | 12/2011 | Djupesland |
| 2012/0000459 A1 | 1/2012 | Djupesland |
| 2012/0006323 A1 | 1/2012 | Djupesland |
| 2012/0073571 A1 | 3/2012 | Djupesland |
| 2012/0090608 A1 | 4/2012 | Djupesland et al. |
| 2012/0260915 A1 | 10/2012 | Djupesland |
| 2013/0098362 A1 | 4/2013 | Djupesland et al. |
| 2013/0125889 A1 | 5/2013 | Djupesland et al. |
| 2013/0327320 A1 | 12/2013 | Djupesland |
| 2014/0018295 A1 | 1/2014 | Djupesland |
| 2014/0041660 A1 | 2/2014 | Djupesland et al. |
| 2014/0060536 A1 | 3/2014 | Djupesland |
| 2014/0073562 A1 | 3/2014 | Djupesland |
| 2014/0144442 A1 | 5/2014 | Djupesland et al. |
| 2014/0144443 A1 | 5/2014 | Djupesland et al. |
| 2014/0166008 A1 | 6/2014 | Djupesland |
| 2014/0202456 A1 | 7/2014 | Djupesland |
| 2014/0246022 A1 | 9/2014 | Djupesland et al. |
| 2015/0007811 A1 | 1/2015 | Djupesland et al. |
| 2015/0013670 A1 | 1/2015 | Djupesland et al. |
| 2015/0013677 A1 | 1/2015 | Djupesland et al. |
| 2015/0053201 A1 | 2/2015 | Djupesland et al. |
| 2015/0090259 A1 | 4/2015 | Djupesland et al. |
| 2015/0101605 A1 | 4/2015 | Djupesland et al. |
| 2015/0144129 A1 | 5/2015 | Djupesland et al. |
| 2015/0165139 A1 | 6/2015 | Hafner |
| 2015/0182709 A1 | 7/2015 | Djupesland |
| 2015/0246194 A1 | 9/2015 | Djupesland et al. |
| 2015/0367090 A1 | 12/2015 | Djupesland et al. |
| 2015/0367091 A1 | 12/2015 | Djupesland et al. |
| 2016/0001022 A1 | 1/2016 | Djupesland et al. |
| 2016/0045687 A1 | 2/2016 | Djupesland |
| 2016/0051778 A1 | 2/2016 | Djupesland et al. |
| 2016/0074603 A1 | 3/2016 | Djupesland et al. |
| 2016/0082206 A1 | 3/2016 | Djupesland et al. |
| 2016/0082207 A1 | 3/2016 | Djupesland et al. |
| 2016/0095993 A1 | 4/2016 | Djupesland |
| 2016/0166788 A1 | 6/2016 | Djupesland et al. |
| 2016/0184537 A1 | 6/2016 | Djupesland |
| 2016/0193435 A1 | 7/2016 | Djupesland |
| 2016/0250408 A1 | 9/2016 | Djupesland |
| 2016/0263334 A1 | 9/2016 | Djupesland |
| 2016/0279357 A1 | 9/2016 | Djupesland |
| 2016/0310683 A1 | 10/2016 | Djupesland et al. |
| 2016/0331916 A1 | 11/2016 | Djupesland et al. |
| 2016/0367771 A1 | 12/2016 | Djupesland |
| 2016/0367772 A1 | 12/2016 | Djupesland |
| 2016/0367774 A1 | 12/2016 | Djupesland et al. |
| 2017/0043108 A1 | 2/2017 | Djupesland et al. |
| 2017/0151397 A1 | 6/2017 | Djupesland |

FOREIGN PATENT DOCUMENTS

| | | | |
|---|---|---|---|
| GB | 2162522 | 2/1986 | |
| GB | 2 400 565 A | 10/2004 | |
| GB | 2404867 | 2/2005 | |
| GB | 2405350 | 3/2005 | |
| GB | 2405800 | 3/2005 | |
| GB | 2418147 | 3/2006 | |
| GB | 2418147 A * | 3/2006 | ........ A61M 15/0028 |
| GB | 2424587 | 10/2006 | |
| WO | WO 96/22802 | 8/1996 | |
| WO | WO 98/53869 | 12/1998 | |
| WO | WO 00/51672 | 9/2000 | |
| WO | WO 01/97689 | 12/2001 | |
| WO | WO 02/068029 | 9/2002 | |
| WO | WO 02/068030 | 9/2002 | |
| WO | WO 02/068031 | 9/2002 | |
| WO | WO 02/068032 | 9/2002 | |
| WO | WO 03/000310 | 1/2003 | |
| WO | WO 03/020350 | 3/2003 | |
| WO | WO 03/082393 | 10/2003 | |
| WO | WO 03/084591 | 10/2003 | |
| WO | WO 03/090812 | 11/2003 | |
| WO | WO 2004/004814 | 1/2004 | |
| WO | WO 2004/004922 | 1/2004 | |
| WO | WO 2004/060433 | 7/2004 | |
| WO | WO 2004/103447 | 12/2004 | |
| WO | WO 2005/016423 | 2/2005 | |
| WO | WO 2005/021059 | 3/2005 | |
| WO | WO-2005021059 A2 * | 3/2005 | ............ A61M 15/00 |
| WO | WO 2006/016530 | 2/2006 | |
| WO | WO 2006/030210 | 3/2006 | |
| WO | WO 2006/090149 | 8/2006 | |
| WO | WO 2006/124954 | 11/2006 | |
| WO | WO 2007/083073 | 7/2007 | |
| WO | WO 2007/093784 | 8/2007 | |
| WO | WO 2007/093791 | 8/2007 | |
| WO | WO 2007/099361 | 9/2007 | |
| WO | WO 2007/102089 | 9/2007 | |
| WO | WO 2007/107887 | 9/2007 | |
| WO | WO 2007/125318 | 11/2007 | |
| WO | WO 2007/141541 | 12/2007 | |
| WO | WO 2008/012531 | 1/2008 | |
| WO | WO 2008/065403 | 6/2008 | |
| WO | WO 2008/081326 | 7/2008 | |
| WO | WO 2008/081327 | 7/2008 | |
| WO | WO 2008/122791 | 10/2008 | |
| WO | WO 2008/122795 | 10/2008 | |
| WO | WO 2009/044172 | 4/2009 | |
| WO | WO 2010/029441 | 3/2010 | |
| WO | WO 2012/035427 | 3/2012 | |
| WO | WO 2012/123819 | 9/2012 | |
| WO | WO 2013/124491 | 8/2013 | |
| WO | WO 2013/124492 | 8/2013 | |
| WO | WO 2013/124493 | 8/2013 | |
| WO | WO 2014/155192 | 10/2014 | |

OTHER PUBLICATIONS

Edvinsson et al., *Triptan-induced contractile (5-HT1B receptor) responses in human cerebral and coronary arteries: relationship to clinical effect*, 109 Clinical Science 335-342 (2005).

Chen et al., *Intranasal absorption of rizatriptan- in vivo pharmacokinetics and bioavailability study in humans.* Pharmazie 60: 39-41 (2005).

Fox, *Onset of Effect of 5-HT JBIID Agonists: A Model With Pharmacokinetic Validation.* Headache 2004; 44:142-147.

Lewis et al., *Inhaled Product Characterization Calculating Particle-Size Distribution Metrics.* Pharmaceutical Technology Nov. 2011.

Wang et al., *Uptake and biodistribution of rizatriptan to blood and brain following different routes of administration in rats.* International Journal of Pharmaceutics 337 (2007) 155-160.

Cindy H. Dubin, *Nothing to Sneeze At*, Pharmaceutical Formulation & Quality Magazine (Jan. 29, 2003).

Per Gisle Djupesland, *Nasal Delivery of Vaccines*, EPC (Jan. 29, 2003).

Per Gisle Djupesland, *Who Nose How Far Nasal Delivery Can Go?*, EPC (Oct. 7, 2003).

Per Gisle Djupesland, *Bi-directional Nasal Drug Delivery*, Innovations in Pharmaceutical Technology (Jul. 10, 2004).

P.G. Djupesland, *Bi-Directional Nasal Delivery of Aerosols Can Prevent Lung Deposition*, Journal of Aerosol Medicine (Sep. 2004).

*Bi-Directional Nasal Device Delivers Drug on Exhalation*, Pharmaceutical Technology (Sep. 10, 2004).

Ola Dale et al., *Intranasal Midazolam: A Comparison of Two Delivery Devices in Human Volunteers*, Journal of Pharmacy and Pharmacology (Oct. 2004).

G. Furness, *Nasal Drug Delivery: Rapid Onset Via A Convenient Route*, ONdrugDelivery Ltd. (2005).

M. Kleven, *Using Computational Fluid Dynamics (CFD) to Improve the Bi-Directional Nasal Drug Delivery Concept*, Trans IChemE Part C. (Jun. 2005).

(56) References Cited

OTHER PUBLICATIONS

Per Gisle Djupesland, *Breath-Actuated Bi-Directional Delivery Sets the Nasal Market on a New Course*, ONdrugDelivery (Oct. 10, 2005).
Hilde Bakke et al., *Oral Spray Immunization May be An Alternative to Intranasal Vaccine Delivery to Induce Systemic Antibodies But Not Nasal Mucosal or Cellular Immunity*, Scan J. of Immunol. (Mar. 2006).
P.G. Djupesland et al., *Breath Actuated Nasal Device Improves Delivery to Target Sites Beyond the Nasal Valve*, The Laryngoscope (Mar. 2006).
R. Luthringer et al., *Rapid Absorption of Sumatriptan Powder and Effects on Glyceryl tinitrate Model of Headache Following Intranasal Delivery Using A Novel Bi-Directional Device*, Journal of Pharmacy and Pharmacology (Jan. 2009).
A. Skretting et al., *A New Method for Scintigraphic Quantification of Deposition and Clearance in Anatomical Regions of the Human Nose*, Nuclear Medicine Communications (Aug. 2009).
Vlckovia et al., *Effective Treatment Of Mild-to-Moderate Nasal Polyposis with Fluticasone Delivered By A Novel Device*, Rhinology (Oct. 22, 2009).
Per Gisle Djupesland et al., *Impact of Baseline Nasal Polyp Size and Previous Surgery on Efficacy of Fluticasone Delivered With a Novel Device: A Subgroup Analysis*, Am. J. Rhinology Allergy (2010).
P.G. Djupesland et al., *Intranasal Sumatriptan Powder Delivered by a Novel Breath Actuated Bi-Directional Device for the Acute Treatment of Migraine: A Randomised Placebo-Controlled Study*, Cephalalgia (Mar. 17, 2010).
F.S. Hansen et al., *Preliminary Efficacy of Fluticasone Delivered By a Novel Device in Recalcitrant Chronic Rhinosinusitis*, Rhinology (Jun. 26, 2010).
Per Gisle Djupesland, *Nasal Drug Delivery Devices: Characteristics and Performance in Clinical Perspective—A Review*, Drug. Deliv. and Transl. Res. (Oct. 18, 2012).
Per Gisle Djupesland, *Nasal Deposition and Clearance in Man: Comparison of a Bidirectional Powder Device and a Traditional Liquid Spray Pump*, Journal of Aerosol Medicine and Pulmonary Drug Delivery (Nov. 2012).
Stewart J. Tepper, *Clinical Implications for Breath-Powered Powder Sumatriptan Intranasal Treatment*, Headache, The American Headache Society (Apr. 29, 2013).
Mohammad Obaidi et al., *Improved Pharmacokinetics of Sumatriptan With Breath Powered Nasal Delivery of Sumatriptan Powder*, Headache, The American Headache Society (May 24, 2013).
Per Gisle Djupesland, *Breath Powdered Nasal Delivery: A New Route to Rapid Headache Relief*, Headache, The American Headache Society (Jun. 4, 2013).
Per Gisle Djupesland et al., *The Nasal Approach to Delivering Treatment for Brain Diseases: An Anatomic, Physiologic, and Delivery Technology Overview*, Therapeutic Delivery (2014).
R.K. Cady et al., *A Randomized Double-Blind, Placebo Controlled Study of Breath Powered Nasal Delivery of Sumatriptan Powder (AVP-825) in the Treatment of Acute Migraine (The TARGET Study)*, Headache (Sep. 8, 2014).
S.J. Tepper et al., *AVP-825 Breath-Powdered Intranasal Delivery System Containing 22 mg Sumatriptan Powder vs. 100 mg Oral Sumatripta in the Acute Treatment of Migraines (The COMPASS Study): A Comparative Randomized Clinical Trial Across Multiple Attacks*, Headache: The Journal of Head and Face Pain (Mar. 29, 2015).
D. S. Quintana et al., *Low-dose Oxytocin Delivered Intranasally with Breath Powdered Device Affects Social-Cognitive Behavior: A Randomized Four-Way Crossover Trial with Nasal Cavity Dimension Assessment*, Transl Psychiatry (Jul. 14, 2015).
R. Mahmoud, *Breathe Out*, Innovations in Phar, Tech. (Dec. 10, 2015).

* cited by examiner

NASAL ADMINISTRATION

This application is a continuation of application No. 12/594,365, filed Apr. 30, 2010, which is a national stage of International Application No. PCT/GB2008/001226, filed Apr. 7, 2008, which claims priority to Great Britain Application No. 0706744.0, filed Apr. 5, 2007. The disclosures of all applications cited in this paragraph are incorporated herein in their entirety by reference.

The present invention relates to the nasal administration of powdered substances, in particular drugs, and in particular substances which require a rapid onset of action, such as in the treatment of pain, including headaches, for example, cluster headaches and migraine, and neuropathic pain.

Referring to FIG. 1(a), the nasal airway 1 comprises the two nasal cavities separated by the nasal septum, which airway 1 includes numerous ostia, such as the paranasal sinus ostia 3 and the tubal ostia 5, and olfactory cells, and is lined by the nasal mucosa. The nasal airway 1 can communicate with the nasopharynx 7, the oral cavity 9 and the lower airway 11, with the nasal airway 1 being in selective communication with the anterior region of the nasopharynx 7 and the oral cavity 9 by opening and closing of the oropharyngeal velum 13. The velum 13, which is often referred to as the soft palate, is illustrated in solid line in the closed position, as achieved by providing a certain positive pressure in the oral cavity 9, such as achieved on exhalation through the oral cavity 9, and in dashed line in the open position.

The present inventors have surprisingly identified that a rapid systemic uptake can be achieved, as compared to the conventional delivery of an equivalent liquid substance, by the delivery of a powdered substance to the posterior region of the nasal airway, and in particular the upper posterior two thirds.

The posterior region of the nasal airway is that region which is posterior of the nasal valve NV, as illustrated in FIG. 1(b). The nasal valve comprises the anterior bony cavum which contains inferior turbinate erectile tissue and septal erectile tissue, which are supported respectively by compliant ala tissue and the rigid cartilaginous septum (Cole, P (The Respiratory Role of the Upper Airways, a selective clinical and pathophysiological review. 1993, Mosby-Year Book Inc. ISBN1.55664-390-X)). These elements combine to form a dynamic valve, which extends over several millimetres, that adjusts nasal airflow, and is stabilized by cartilage and bone, modulated by voluntary muscle and regulated by erectile tissue. The lumen of the nasal valve is the section of narrowest cross-sectional area between the posterior and anterior regions of the nasal airway, and is much longer and narrower dorsally than ventrally, and this lumen defines a triangular entrance which extends to the piriform region of the bony cavum. The nasal valve is lined in its anterior part with transitional epithelium, with a gradual transition posterior to respiratory epithelium. The nasal valve and anterior vestibule define roughly the anterior one-third of the nose.

The posterior region of the nasal airway is that region which is lined with respiratory epithelium, which is ciliated, and olfactory epithelium, which comprises nerves which extend downwards through the cribiform plate CP from the olfactory bulb, whereas the anterior region of the nasal airway is that region which is lined with squamous epithelium, which is not ciliated, and transitional epithelium. The olfactory epithelium extends on both the lateral and medial sides of the nasal airway, and typically extends downwards about 1.5 to 2.5 cm.

The upper posterior region is the region above the inferior meatus IM, as illustrated in FIG. 1(b), and encompasses the middle turbinate, the sinus ostia in infundibulum (ostia to maxillary, frontal and ethmoidal sinuses), the olfactory region, and the upper branches of the trigeminal nerve, and is that region which includes veins which drain to the venous sinuses that surround the brain.

As illustrated in FIG. 1(b), the posterior region of the nasal airway is the nasal region posterior of an imaginary vertical plane VERT1 which is located at a position corresponding to one-quarter of the distance between the anterior nasal spine AnS, which is a pointed projection at the anterior extremity of the intermaxillary suture, and the posterior nasal spine PnS, which is the sharp posterior extremity of the nasal crest of the hard palate and represents the transition between the nose and the nasopharynx, which corresponds to a distance posterior of the anterior nasal spine AnS of between about 13 mm and about 14 mm (Rosenberger, H (Growth and Development of the Naso-Respiratory Area in Childhood, PhD Thesis, Laboratory of Anatomy, School of Medicine, Western Reserve University, Presented to the Annual Meeting of the American Laryngological, Rhinological and Otological Society, Charleston, S.C., USA, 1934) defines the distance between the anterior nasal spine AnS and the posterior nasal spine PnS as being 56 mm in eighteen year old boys and 53.3 mm in eighteen year old girls). As again illustrated in FIG. 1(b), the posterior nasal region is bounded posteriorly by an imaginary vertical plane VERT2 which extends through the posterior nasal spine PnS.

As further illustrated in FIG. 1(b), the upper region of the nasal airway is an upper segment of the nasal airway which is bounded by the cribiform plate CP and a horizontal plane HORIZ which is located at a position corresponding to one-third of the distance between the nasal floor NF of the nasal airway and the cribiform plate CP, which corresponds to a height of typically between about 13 and about 19 mm above the nasal floor NF (Zacharek, M A et al (Sagittal and Coronal Dimensions of the Ethmoid Roof: A Radioanatomic Study, Am J Rhinol 2005, Vol 19, pages 348 to 352) define the distance from the nasal floor NF to the cribiform plate CP as 46+/−4 mm).

The upper posterior region is thus that upper posterior region which is bounded by the above-defined vertical and horizontal planes VERT1, HORIZ.

The prior art includes a number of comparative studies which compare the pharmacokinetics of substances which are delivered intranasally as liquids and powders. Examples of such studies include the following.

Marttin et al (Nasal absorption of dihydroergotamine from liquid and powder formulations in rabbits, J. Pharm. Sci., 86(7), pages 802 to 807, 1997) compared powder and liquid formulations of dihydroergotamine which contained cyclodextrins, and reported the time maximum plasma concentration $T_{max}$ to be broadly comparable for a range of powder and liquid formulations.

Matsuyama et al (Improved nasal absoprtion of salmon calcitonin by powdery formulation with N-acetyl-L-cysteine as a mucolytic agent, J. Cont. Rel., 115, pages 183 to 188, 2006) compared the intranasal administration of powders and liquids with and without N acetyl cysteine in rats. The powder formulations used in these studies contained ethylcellulose and sodium glycocholate as absorption enhancers, and, despite the use of these absorption enhancers, in the formulations lacking N acetyl cysteine, there was no apparent difference in the time maximum plasma concentration $T_{max}$ between the powder and liquid formulations.

Schipper et al (Nasal insulin delivery with dimethyl beta cyclodextrin as an absorption enhancer in rabbits: powder more effective than liquid formulations, Pharm. Res., 10, pages 682 to 686, 1993) compared the intranasal administration of powders and liquids containing dimethyl beta cyclodextrin as an absorption enhancer, and determined the peak plasma concentration $C_{max}$ for the powder formulation to be greater than that for the liquid formulation.

Resta et al (A comparison of sodium cromoglycate nasal solution and powder in the treatment of allergic rhinitis, Br. J. Clin. Pract., 46, pages 94 to 98, 1992) compared the intranasal administration of powder and solution formulations of sodium cromoglycate in humans, and determined the powder formulation to be somewhat more effective.

Pontiroli et al (Nasal administration of glucagons and human calcitonin to healthy subjects: a comparison of powders and spray solutions and of different enhancing agents, Eur. J. Clin. Pharmacol., 37, pages 427 to 430, 1989) compared the intranasal administration of liquid and powder formulations of calcitonin in humans and determined that the absorption was comparable in these formulations.

Ishikawa et al (Insoluble Powder Formulation as an Effective Nasal Drug Delivery System, Int. J. Pharm., 224, pages 105 to 114, 2001) reported that that permeability of powder and liquid formulations of elcatonin across excised rabbit mucosa was comparable. In vivo, the powder formulation gave greater bio-availability, which was attributed to the use of insoluble calcium carbonate in delaying residence time.

The prior art also teaches that the use of powdered substances can lead to reduced bio-availability, which would be understood as a clear prejudice to the use of powdered substances.

Callens et al (Influence of multiple nasal administrations of bio-adhesive powders on the insulin BA, Int. J. Pharm., 250, pages 415 to 422, 1993) studied the intranasal administration of insulin powders and attributes the longer residence times of powder formulations as being disadvantageous, particularly after multiple administrations, in leading to reduced bio-availability.

The prior art also studies the effect of deposition in anterior and posterior regions of the nasal airway.

Pringels et al (Influence of deposition and spray pattern of nasal powders on insulin bioavailability, Int. J. Pharm., 310(1-2), pages 1 to 7, 2006) compared the bioavailability of insulin powders, in a starch formulation, which was delivered to rabbits and reported that deposition posterior to the nasal valve resulted in lower bio-availability than anterior deposition.

This teaching is to the delivery of powdered substances to the anterior region of the nasal cavity, in order to provide for improved bio-availability, and is contrary to the present invention.

In terms of general considerations regarding nasal drug delivery, Behi et al (Effects of physiochemical properties and other factors on systemic nasal drug delivery, Advanced Drug Delivery Reviews, 29, pages 89 to 116, 1998) provides a comprehensive review of systemic nasal drug delivery.

Also, McMartin, C et al (Analysis of Structural Requirements for the Absorption of Drugs and Macromolecules from the Nasal Cavity, J. Pharm. Sci., 76(7), 1987, pages 535 to 540) provides a general review of the nasal administration of drugs, in particular those drugs which cannot be given orally because of linkages which are polar or susceptible to degradation in the GI tract. This review concludes that drugs of up to a molecular weight of 1000 should be administrable without the use of adjuvants, and that this property could be used for the administration of polar drugs, for example, peptides.

In one aspect the present invention provides a delivery device for delivering a powdered substance to the posterior region of a nasal cavity of a subject, the delivery device comprising: a nosepiece for insertion into a nasal cavity of a subject through which a powdered substance is delivered to the posterior region of the nasal cavity of the subject; and a substance supply unit which is operable to deliver a powdered substance through the nosepiece.

In one embodiment the substance supply unit comprises a container-receiving unit which comprises a container chamber for receiving a substance-containing container which contains a powdered substance to be delivered to the nasal cavity of the subject, and the container chamber includes an outlet which is in fluid communication with the nosepiece such as to provide for delivery of the powdered substance from the container chamber to the nosepiece.

In one embodiment the container comprises a capsule.

In one embodiment the capsule is formed from a cellulose derivative, and preferably hydroxypropyl methylcellulose (HPMC).

In another embodiment the capsule is formed from a gelatine derivative.

In one embodiment the capsule is coated with a hydrophobic material, and preferably parylene.

In one embodiment the nosepiece is configured, when inserted into the nasal cavity, to extend into the nasal valve and provide for expansion thereof.

In one embodiment the nosepiece is configured such as to obstruct the nasal valve.

In one embodiment the nosepiece is configured such as to close the nasal valve, and thereby substantially prevent deposition of substance anteriorly of the same.

In one embodiment the delivery device further comprises: a mouthpiece through which the subject in use exhales to cause closure of the oropharyngeal velum of the subject.

In one embodiment the delivery device further comprises: a flow channel fluidly connecting the nosepiece and the mouthpiece, whereby exhaled air from an exhalation breath is delivered through the nosepiece.

In one embodiment the container chamber includes an inlet which is fluidly connected to the mouthpiece, such that exhaled air from an exhalation breath acts to entrain powdered substance as contained by the container and deliver the same through the nosepiece.

In one embodiment the container-containing member includes a flow passage in which the container is disposed, such as to be rotatable therewithin when an air flow is delivered therethrough.

In another embodiment the delivery device further comprises: a flow channel fluidly connected to the nosepiece through which a gas flow, separate to an exhaled air flow from an exhalation breath of the subject, is in use delivered to the nosepiece; and a gas supply unit for supplying a gas flow to the flow channel.

Preferably, the delivery device is configured such that at least 55% of the dose as initially deposited in the nasal cavity is deposited in the region posterior of the nasal valve.

More preferably, the delivery device is configured such that at least 60% of the dose as initially deposited in the nasal cavity is deposited in the region posterior of the nasal valve.

Yet more preferably, the delivery device is configured such that at least 65% of the dose as initially deposited in the nasal cavity is deposited in the region posterior of the nasal valve.

Still more preferably, the delivery device is configured such that at least 70% of the dose as initially deposited in the nasal cavity is deposited in the region posterior of the nasal valve.

Still yet more preferably, the delivery device is configured such that at least 80% of the dose as initially deposited in the nasal cavity is deposited in the region posterior of the nasal valve.

Preferably, the delivery device is configured such that at least 35% of the dose as initially deposited in the nasal cavity is deposited in the upper posterior two thirds thereof.

More preferably, the delivery device is configured such that at least 40% of the dose as initially deposited in the nasal cavity is deposited in the upper posterior two thirds thereof.

Yet more preferably, the delivery device is configured such that at least 45% of the dose as initially deposited in the nasal cavity is deposited in the upper posterior two thirds thereof.

Still more preferably, the delivery device is configured such that at least 50% of the dose as initially deposited in the nasal cavity is deposited in the upper posterior two thirds thereof.

Yet still more preferably, the delivery device is configured such that at least 55% of the dose as initially deposited in the nasal cavity is deposited in the upper posterior two thirds thereof.

In one embodiment the powdered substance contains substantially entirely active substance and no introduced excipients, and in particular adjuvants.

In one embodiment the powdered substance has a pH of between about 4.5 and about 5.3, and preferably about 4.8.

In one embodiment the powdered substance has a particle size distribution of 10% less than about 20 µm, 50% less than about 50 µm and 90% less than about 150 µm, and preferably 10% less than about 10 µm, 50% less than about 30 µm and 90% less than about 90 µm.

In one embodiment the powdered substance has an untapped bulk density of between about 0.3 g/ml and about 0.5 g/ml, and preferably about 0.4 g/ml.

In one embodiment the powdered substance has a tapped bulk density of between about 0.5 g/ml and about 0.75 g/ml, and preferably about 0.63 g/ml.

In another aspect the present invention provides a method of delivering a powdered substance to the posterior region of a nasal cavity of a subject, the method comprising the steps of: fitting a nosepiece to a nasal cavity of a subject; and delivering a powdered substance through the nosepiece to the posterior region of the nasal cavity of the subject.

In one embodiment the powdered substance is delivered from a container chamber which houses a container which contains a powdered substance to be delivered to the nasal cavity of the subject, and the container chamber includes an outlet which is in fluid communication with the nosepiece such as to provide for delivery of the powdered substance from the container chamber to the nosepiece.

In one embodiment the container comprises a capsule.

In one embodiment the capsule is formed from a cellulose derivative, and preferably hydroxypropyl methylcellulose (HPMC).

In another embodiment the capsule is formed from a gelatine derivative.

In one embodiment the capsule is coated with a hydrophobic material, and preferably parylene.

In one embodiment the nosepiece is configured, when inserted into the nasal cavity, to extend into the nasal valve and provide for expansion thereof.

In one embodiment the nosepiece is configured such as to obstruct the nasal valve.

In one embodiment the nosepiece is configured such as to close the nasal valve, and thereby substantially prevent deposition of substance anteriorly of the same.

In one embodiment the method further comprises the step of: closing the oropharyngeal velum of the subject.

In one embodiment the method further comprises the step of: the subject exhaling through a mouthpiece to cause closure of the oropharyngeal velum of the subject.

In one embodiment the mouthpiece is fluidly connected to the nosepiece, whereby exhaled air from an exhalation breath is delivered through the nosepiece.

In one embodiment the container chamber includes an inlet which is fluidly connected to the mouthpiece, such that exhaled air from an exhalation breath acts to entrain powdered substance as contained by the container and deliver the same through the nosepiece.

In one embodiment the container chamber includes a flow passage in which the container is disposed, such as to be rotatable therewithin when an air flow is delivered therethrough.

In another embodiment the method further comprises the step of: delivering a gas flow, separate to an exhaled air flow from an exhalation breath of the subject, to the nosepiece.

Preferably, at least 55% of the dose as initially deposited in the nasal cavity is deposited in the region posterior of the nasal valve.

More preferably, at least 60% of the dose as initially deposited in the nasal cavity is deposited in the region posterior of the nasal valve.

Yet more preferably, at least 65% of the dose as initially deposited in the nasal cavity is deposited in the region posterior of the nasal valve.

Still more preferably, at least 70% of the dose as initially deposited in the nasal cavity is deposited in the region posterior of the nasal valve.

Yet still more preferably, at least 80% of the dose as initially deposited in the nasal cavity is deposited in the region posterior of the nasal valve.

Preferably, at least 35% of the dose as initially deposited in the nasal cavity is deposited in the upper posterior two thirds thereof.

More preferably, at least 40% of the dose as initially deposited in the nasal cavity is deposited in the upper posterior two thirds thereof.

Yet more preferably, at least 45% of the dose as initially deposited in the nasal cavity is deposited in the upper posterior two thirds thereof.

Still more preferably, at least 50% of the dose as initially deposited in the nasal cavity is deposited in the upper posterior two thirds thereof.

Yet still more preferably, at least 55% of the dose as initially deposited in the nasal cavity is deposited in the upper posterior two thirds thereof.

In one embodiment the powdered substance contains substantially entirely active substance and no introduced excipients, and in particular adjuvants.

In one embodiment the powdered substance has a pH of between about 4.5 and about 5.3, and preferably about 4.8.

In one embodiment the powdered substance has a particle size distribution of 10% less than about 20 µm, 50% less than about 50 µm and 90% less than about 150 µm, and preferably 10% less than about 10 µm, 50% less than about 30 µm and 90% less than about 90 µm.

In one embodiment the powdered substance has an untapped bulk density of between about 0.3 g/ml and about 0.5 g/ml, and preferably about 0.4 g/ml.

In one embodiment the powdered substance has a tapped bulk density of between about 0.5 g/ml and about 0.75 g/ml, and preferably about 0.63 g/ml.

In one embodiment the time maximum plasma concentration $T_{max}$ is less than about 25 minutes.

In one embodiment the time maximum plasma concentration $T_{max}$ is less than about 20 minutes.

In one embodiment the peak plasma concentration $C_{max}$ for the active substance is at least 10 ngml$^{-1}$ for a 10 mg dose of the active substance.

In one embodiment the peak plasma concentration $C_{max}$ for the active substance is at least 15 ngml$^{-1}$ for a 20 mg dose of the active substance.

Preferably, the ratio of the nasal absorption fraction to total bio-availability (BA) is greater than about 1.

More preferably, the ratio of the nasal absorption fraction to total bio-availability (BA) is greater than about 1.5.

Yet more preferably, the ratio of the nasal absorption fraction to total bio-availability (BA) is greater than about 2.0.

In one embodiment the powdered substance comprises a triptan.

In one embodiment the powdered substance comprises sumatriptan.

In another embodiment the powdered substance comprises one or more of risatriptan, naratriptan, eletriptan, frovatriptan and zolmitriptan.

In another embodiment the powdered substance comprises an analgesic.

In one embodiment the powdered substance comprises an opiod.

In another embodiment the powdered substance comprises an ergotamine, such as one or more of dihydroergotamine mesylate, ergonovine maleate and ergotamine tartarate with caffeine.

In a further embodiment the powdered substance comprises one or more of fentanyl, oxycondone, hydromorphone, morphine, codeine, ketobemidone and cocaine.

In a further embodiment the powdered substance comprises a benzodiazepine, such as midazolam.

In a yet further embodiment the powdered substance comprises a non-steroidal anti-inflammatory drug (NSAID), such as one or more of aspirin, ibuprofen, naproxen, indomethacin, diclofenac and ketoprofen.

In a still further embodiment the powdered substance comprises a peptide or protein.

In one embodiment the peptide or protein has a molecular weight greater than about 1000.

In one embodiment the powdered substance comprises one or more of insulin, including its analogues and derivatives, desmopressin and calcitonin.

In a yet still further embodiment the powdered substance comprises one or more of a vaccine, an immunomodulator and an immunostimulator.

In one embodiment the method is for the treatment of pain.

In one embodiment the method is for the treatment of headaches.

In one embodiment the method is for the treatment of cluster headaches.

In another embodiment the method is for the treatment of migraine.

In another embodiment the method is for the treatment of neuropathic pain.

In another embodiment the method is for inducing sedation.

In a further embodiment the method is for the treatment of a partial or full epilepsy seizure.

In a yet further embodiment the method is for the treatment of a panic disorder.

In a still further embodiment the method is for the treatment of insomnia.

In a still yet further embodiment the method is for the treatment of jet-lag.

In yet another embodiment the method is for regulating blood glucose levels.

In still another embodiment the method is for influencing satiety or the sense of satiety.

In yet still another embodiment the method is for delivering a memory-enhancing agent prior to a learning episode.

The present applicant has developed a novel nasal delivery system, as disclosed in WO-A-2000/051672, the content of which is herein incorporated by reference, which provides for the delivery of drugs and vaccines in a bi-directional air flow through the two nasal passages when connected in series by closure of the oropharyngeal velum.

The present invention will now be described hereinbelow by way of example only with reference to the accompanying drawings, in which:

FIG. 1(a) schematically illustrates the anatomy of the upper respiratory tract of a human subject;

Figure 4:
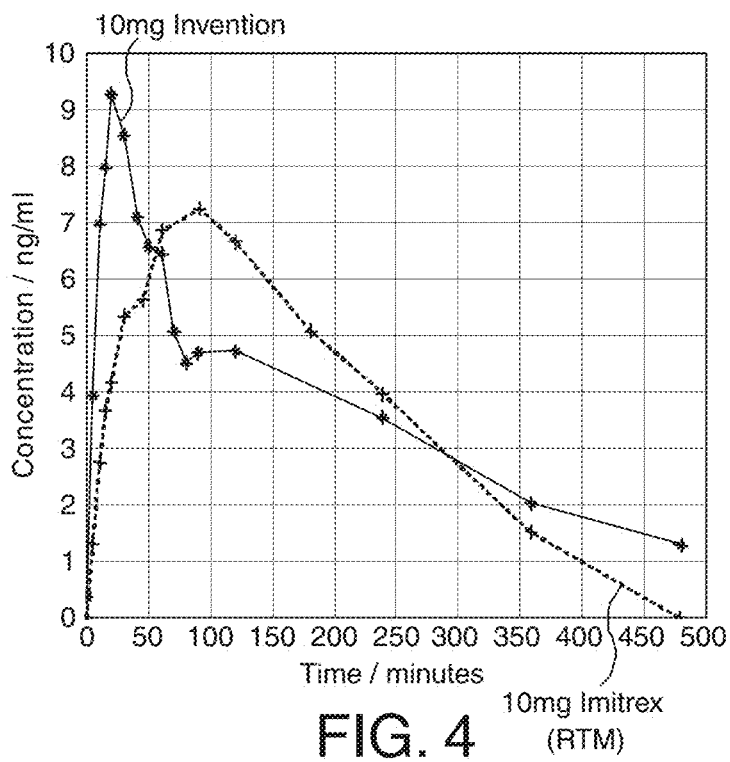
Figure 5:
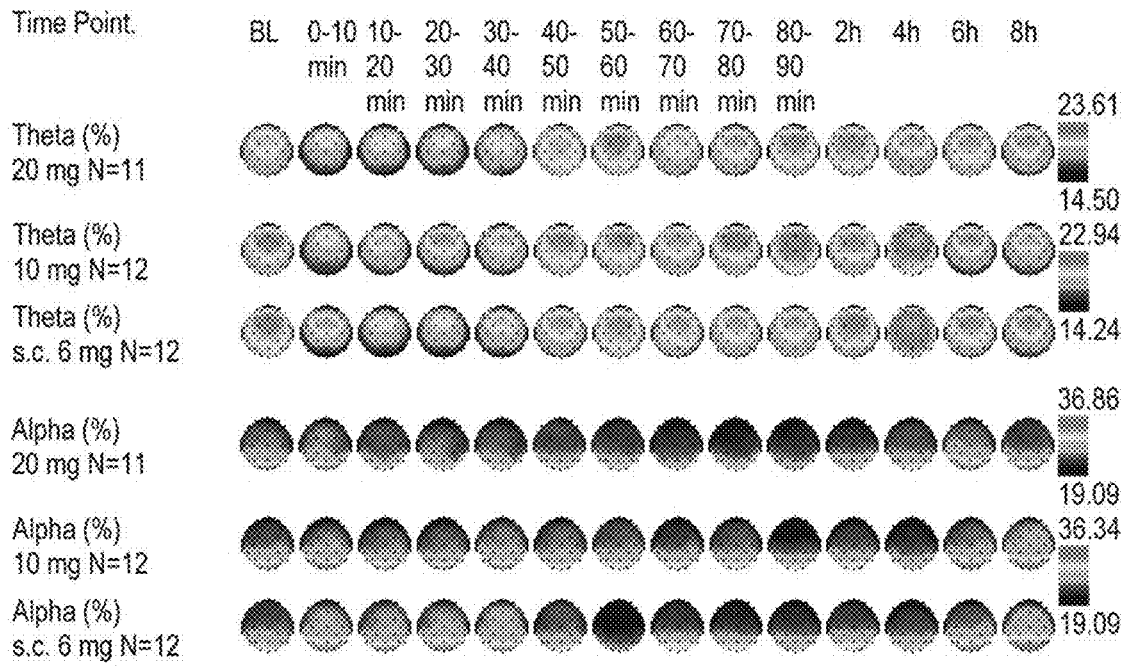

FIG. 4 illustrates the time course for the measured blood plasma concentrations of sumatriptan for the 10 mg intranasal administration of the present invention as employed in Example #1 as compared to historic data for 10 mg Imitrex® intranasal administration; and FIG. 5 illustrates median maps for theta and alpha relative energies for the 10 mg and 20 mg nasal administrations of the present invention and the 6 mg comparator sub-cut administration as employed in Example #1.

Figure 2:
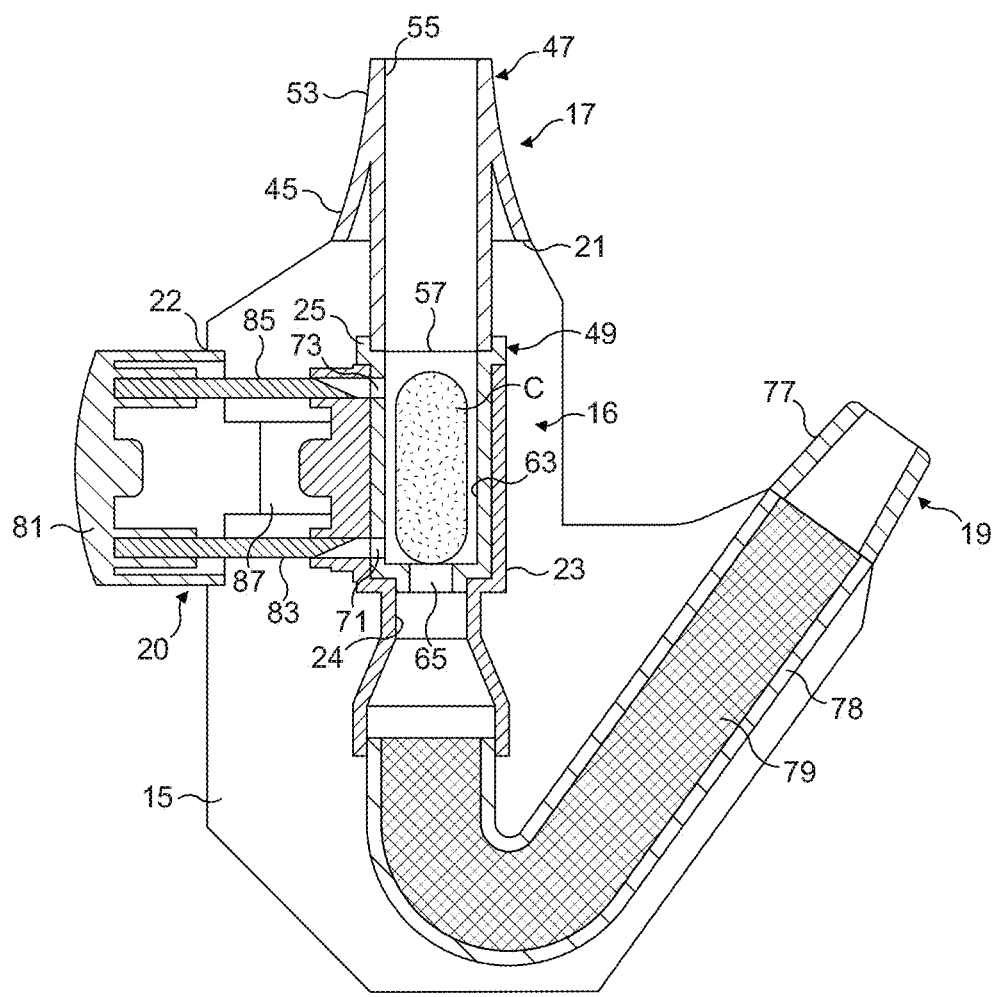
FIG. 2 illustrates a nasal delivery device in accordance with one embodiment of the present invention.
Figure 3:
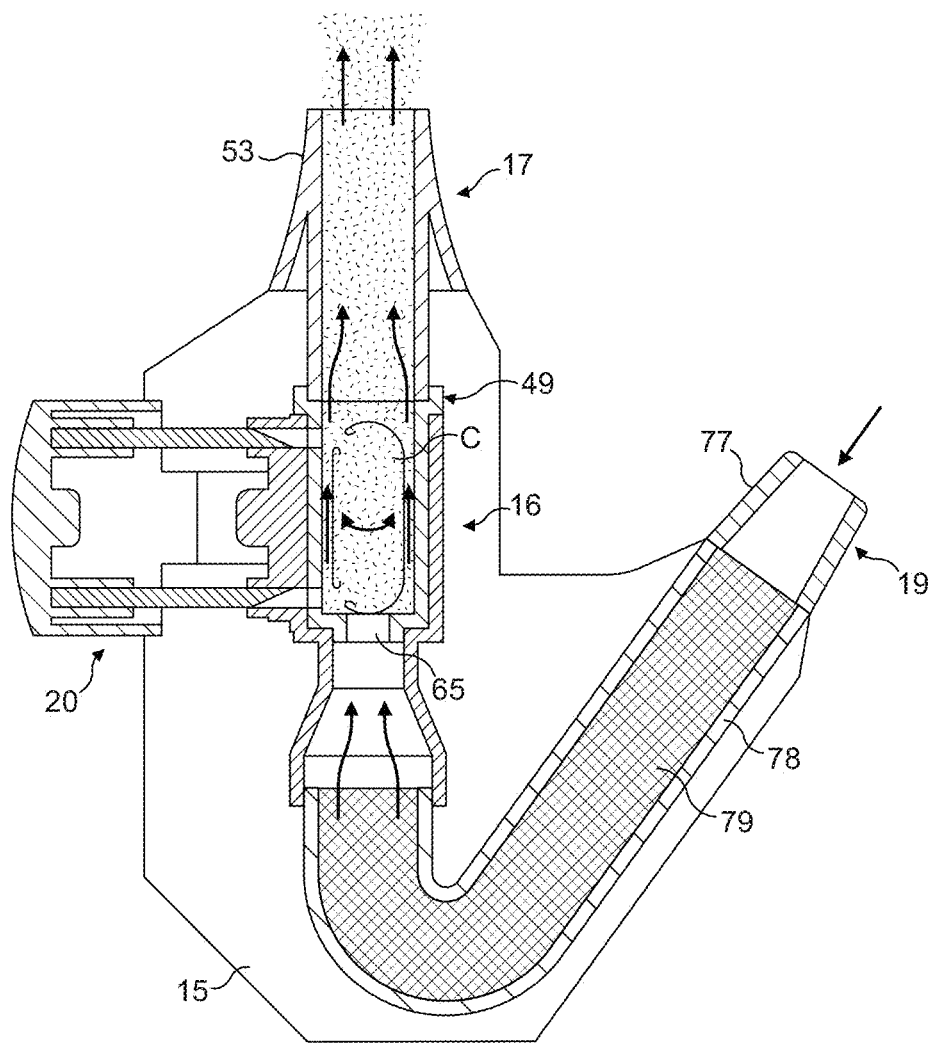
FIG. 3 illustrates the nasal delivery device of FIG. 2, where operative in delivering substance to the nasal cavity of the subject.

FIGS. 2 and 3 illustrate a nasal delivery device in accordance with one embodiment of the present invention.

The delivery device comprises a housing 15, a capsule-receiving unit 16 for receiving a capsule C, a nosepiece unit 17 for fitting to a nasal cavity of a subject, a mouthpiece unit 19 through which the subject exhales, and a capsule-piercing mechanism 20, which is operable to pierce a capsule C as contained by the capsule-receiving unit 16 and thereby prime the delivery device for operation.

The housing 15 includes a first, nosepiece aperture 21, in this embodiment at the upper end of the housing 15, which receives the nosepiece unit 17, and a second, lateral aperture 22, in this embodiment in an end wall of the housing 15, through which extends an actuator button 81 of the capsule-piercing mechanism 20, as will be described in more detail hereinbelow.

The capsule-receiving unit 16 comprises a capsule-receiving member 23, in this embodiment an elongate, upstanding chamber which is disposed opposite the nosepiece aperture 21 in the housing 15, for receiving a capsule C, in this embodiment as contained within a capsule-containing member 49 of the nosepiece unit 17, as will be described in more detail hereinbelow.

In this embodiment the capsule-receiving member 23 includes an inlet 24 and an outlet 25 for providing for an air flow therethrough, with the outlet 25, as defined by an upper, downstream end of the capsule-receiving member 23, being adapted to receive the capsule-containing member 49 of the nosepiece unit 17, such that the capsule-containing member 49 is a sealing fit within the capsule-receiving member 23.

The nosepiece unit 17 comprises a main body member 45 which is configured to fit in the nosepiece aperture 21 of the housing 15, a nosepiece 47 which extends outwardly of the main body member 45 for fitting to the nostril of the subject, and a capsule-containing member 49 which extends inwardly of the main body member 45 and contains a capsule C, the contents of which are to be delivered to the nasal cavity of the subject. In this embodiment the capsule C is a hydroxypropyl methylcellulose (HPMC) capsule which contains a particulate substance, such as a powdered substance, and typically a pharmaceutical substance. In other embodiments the capsule C could be formed substantially of another cellulose derivative, such as hydroxypropylcellulose, methylcellulose, ethylcellulose and carboxymethylcellulose. In an alternative embodiment the capsule C can be formed from a gelatine derivative. In one embodiment the capsule C can be coated with a hydrophobic material, such as parylene.

In this embodiment the nosepiece 47 has a substantially frusto-conical outer section 53 for guiding the nosepiece unit 17 into a nasal passage of the subject and providing a fluid-tight seal with the nares of the nostril, and includes an inner channel 55, here of substantially cylindrical section, through which substance is delivered to a posterior region of the nasal passage of the subject, in this embodiment an upper posterior region as bounded by a vertical plane which is located posterior of the anterior nasal spine AnS at a position corresponding to one-quarter of the distance between the anterior and posterior nasal spines AnS, PnS and a horizontal plane which is located above the nasal floor at a height one-third of the distance between the nasal floor and the cribiform plate. As discussed hereinabove, the present inventors have recognized that an increased delivery of powdered substance to the upper posterior region of the nasal passage surprisingly provides for a very rapid onset of action as compared to the conventional nasal administration of a liquid substance.

In this embodiment the nosepiece 47 is configured to deliver a significant fraction of substance to the upper posterior region of the nasal passage, here an initial deposition of greater than 30% of the delivered dose.

In this embodiment the nosepiece 47, in providing a fluid-tight seal with the nostril of the subject, provides for bi-directional delivery through the nasal airway of the subject, as disclosed in the applicant's earlier WO-A-2000/051672. In another embodiment, however, the nosepiece 47 need not provide a sealing fit, thus encompassing delivery to the nasal cavity, but not necessarily bi-directional delivery.

In this embodiment the nosepiece 47 includes a trap element 57, typically a perforated or mesh element, for preventing any foreign matter, such as a part of the capsule C, which is above a predetermined size from passing through the nosepiece 47 and into the nasal cavity of the subject.

The capsule-containing member 49 includes an elongate flow passage 63, in this embodiment cylindrical in shape, in which the capsule C is oriented axially therealong such as to be rotatable therewithin when an air flow is delivered therethrough, and an inlet aperture 65 in fluid communication with one, the downstream, end of the flow passage 63, which inlet aperture 65 provides a flow restriction to an air flow as delivered therethrough and acts as a seat for one, the lower, end of the capsule C prior to the delivery of an air flow through the flow passage 63.

The capsule-containing member 49 further includes a plurality of, in this embodiment first and second piercing apertures 71, 73 in a lateral wall thereof for enabling the capsule C to be pierced at locations spaced along the axial length thereof. In this embodiment the first, lower aperture 71 is located such that the capsule C is pierced at a location above the height of the dose of substance as contained thereby when the lower end of the capsule C is seated in the inlet aperture 65 of the flow passage 63. In this way, the dose of substance as contained by the capsule C is not released into the flow passage 63 until an air flow is delivered through the flow passage 63.

In this embodiment the nosepiece unit 17 is provided as a replaceable unit which is replaced following each operation of the delivery device. In this embodiment the nosepiece unit 17 can be packaged in air-tight packaging, for example, an aluminum foil package.

The mouthpiece unit 19 comprises a mouthpiece 77, in this embodiment as gripped in the lips of the subject, through which the subject exhales to deliver an entraining air flow through the capsule-receiving unit 16, and an air chamber 78, in this embodiment an elongate tubular section, which fluidly connects the mouthpiece 77 and the capsule-receiving unit 16.

In this embodiment the air chamber 78 has a greater volume than the capsule-receiving member 23 of the capsule-receiving unit 16, and preferably has a volume at least twice that of the capsule-receiving member 23.

In this embodiment the air chamber 78 incorporates a temperature regulator 79, here formed as a condenser for cooling the exhaled air flow, at least at the upstream end thereof. With this configuration, the exhaled air flow is cooled during exhalation.

In this embodiment the temperature regulator 79 comprises a labyrinthine structure. In another embodiment the temperature regulator 79 could be provided by a filter element, which could also act as a microbiological filter.

In one embodiment the temperature regulator 79 could include means for drying the condensate as collected therein when the delivery device is not in use.

In one embodiment the air chamber 78 is removable, such as to allow for cleaning or replacement.

This arrangement has been found to provide for reliable operation of the delivery device, in delivering substance from the capsule C. The present inventors have established that the provision of moist exhaled air directly to the capsule C can sometimes prevent the required rotation of the capsule C, and thereby prevent proper release of the substance as contained thereby.

By providing a volume of cooler air, and arranging for that volume of cooler air to be delivered initially in a burst, the required rotation of the capsule C is seen repeatedly.

The capsule-piercing mechanism 20 comprises an actuator button 81 which extends through the lateral aperture 22 in the housing 15 such as to allow for operation by the subject, a plurality of, in this embodiment first and second piercing elements 83, 85 which are supported by the actuator button 81 and extend forwardly thereof, such that, on depression of the actuator button 81 from a retracted position to an extended position, the piercing elements 83, 85 are driven through respective ones of the piercing apertures 71, 73 in the lateral wall of the capsule-containing member 49 to pierce the capsule C.

In this embodiment the capsule-piercing mechanism 20 includes a resilient element 87 which acts to bias the actuator button 81 outwardly towards the retracted position, such that, following depression of the actuator button 81 to pierce the capsule C, the actuator button 81 is returned to the retracted position. In this embodiment the resilient element 87 is formed as an integral part of the actuator button 81, but in other embodiments could be provided by a separate element, such as a compression spring.

Operation of the delivery device will now be described hereinbelow.

Firstly, taking the delivery device in hand, and with a nosepiece unit 17 inserted in the housing 15, the subject depresses the actuator button 81 of the capsule-piercing mechanism 20 such as to pierce the capsule C as contained in the capsule-containing member 49.

By depressing the actuator button 81, the capsule C is pierced by the piercing elements 83, 85 at two locations spaced along the axial length thereof. In this embodiment the first, lower piercing element 83 acts to pierce the capsule C at a location just above the height of the substance as contained by the capsule C, the capsule C only being part filled, and the second, upper piercing element 85 acts to pierce the upper, distal end of the capsule C.

The actuator button 81 is then released, which causes the actuator button 81 to be returned to the retracted position under the bias of the biasing element 87. In this way, the delivery device is primed and ready for use.

The subject then inserts the nosepiece 47 into one of his/her nasal passages until the nosepiece 47 abuts the nares of the nostril such as to establish a fluid-tight seal therewith, at which point the distal end of the nosepiece 47 extends about 2 cm into the nasal passage of the subject, and grips the mouthpiece 77 in his or her lips.

The subject then begins to exhale through the mouthpiece 47, which exhalation acts to close the oropharyngeal velum of the subject and drive an air flow through the nasal airway of the subject, with the air flow passing into the one nasal passage, around the posterior margin of the nasal septum and out of the other nasal passage, thereby achieving a bi-directional air flow through the nasal airway of the subject.

When the subject exhales with sufficient force, the capsule C is lifted from the seat as defined by the inlet aperture 65 of the capsule-containing member 49 and the capsule C is rotated, which rotation acts to release the substance from within the capsule C which is entrained by the exhaled air flow and delivered to the posterior region of the nasal cavity of the subject.

With continued exhalation, the capsule C continues to rotate.

This operation of the delivery device can be repeated with a new capsule C.

In this embodiment the entire nosepiece unit 17 is replaced, but in other embodiments either the capsule-containing member 49 or just the capsule C could be replaced.

The present invention will now be described hereinbelow with reference to the following non-limiting Examples.

EXAMPLE #1

The purpose of this study was to study the pharmacokinetics of sumatriptan where intranasally delivered using the above-described bi-directional nasal administration system.

In this study, twelve healthy subjects were studied.

In separate sessions, the subjects received 10 mg and 20 mg of sumatriptan base by the bi-directional administration system of the above-described embodiment, from which a powdered sumatriptan formulation was nasally administered, with 20 mg of the sumatriptan base being delivered in two successive 10 mg doses through the respective nostrils of the subjects, and 6 mg of sumatriptan base (IMIGRAN®) Injection pre-filled syringe as available from GlaxoSmithKline) by sub-cut administration.

In this study, the sumatriptan administrations were administered 15 minutes prior to the administration of glyceryltrinitrate (GTN), which allowed the effect on quantitative wake EEG to be studied in subjects suffering from migraine, where GTN is expected to induce migraine in 75% of subjects who have a history of migraine.

The powdered sumatriptan formulation was contained in an HPMC capsule and comprised a 10 mg dose of micronized sumatriptan succinate powder and contained no excipients, such as adjuvants.

The sumatriptan succinate powder has a pH (1% w/v in water) of 4.77. In a preferred embodiment the sumatriptan succinate powder has a pH of between about 4.5 and about 5.3, and preferably about 4.8.

The sumatriptan succinate powder has a particle size distribution of 10% less than 8.08 µm, 50% less than 29.77 µm and 90% less than 88.54 µm.

In a preferred embodiment the sumatriptan succinate powder has a particle size distribution of 10% less than about 20 µm, 50% less than about 50 µm and 90% less than about 150 µm, and preferably 10% less than about 10 µm, 50% less than about 30 µm and 90% less than about 90 µm.

The sumatriptan succinate powder has an untapped bulk density of 0.415 g/ml and a tapped bulk density of 0.632 g/ml. In a preferred embodiment the sumatriptan succinate powder has an untapped bulk density of between about 0.3 g/ml and about 0.5 g/ml, and preferably about 0.4 g/ml. In a preferred embodiment the sumatriptan succinate powder has a tapped bulk density of between about 0.5 g/ml and about 0.75 g/ml, and preferably about 0.63 g/ml.

Venous blood samples, each having a volume of 5 ml, were drawn just prior to administration and at 5, 10, 15, 20, 30, 40, 50, 60, 70, 80, 90, 120, 240, 360, 480 and 720 minutes after administration, and the blood plasma concentration of sumatriptan was determined.

From these measured blood plasma concentrations, average values for the time maximum plasma concentration $T_{max}$, the peak plasma concentration $C_{max}$, the area under the curve (AUC) at times 20, 30, 60 and 120 minutes and ∞, which assumes a zero plasma concentration at 12 hours, and the bio-availability BA were determined for evaluable subjects, as set out in Table I hereinbelow. For comparison, the corresponding pharmacokinetic parameters for the intranasal administration of liquid sumatriptan succinate sprays (10 mg and 20 mg sumatriptan base) (Imitrex® as available from GlaxoSmithKline). The historical data source for the Imitrex® nasal spray is the NDA (#20-626), Study #2a, as submitted by Glaxo Wellcome Inc. to the FDA, USA.

TABLE I

|  | 10 mg Invention | 20 mg Invention | 6 mg Sub-Cut | 10 mg Imitrex | 20 mg Imitrex |
| --- | --- | --- | --- | --- | --- |
| $T_{max}$/min | 20 | 20 | 10 | 90 | 90 |
| $C_{max}$/ng ml$^{-1}$ | 10.5 | 15.9 | 87.4 | 7.2 | 12.8 |
| $C_{20}$/ng ml$^{-1}$ | 10.5 | 15.9 | 66.4 | 4.2 | 7.1 |
| $AUC_{120}$/ng min ml$^{-1}$ | 800 | 1350 | 4473 | 690 | 1182 |
| $AUC\infty$/ng min ml$^{-1}$ | 2137 | 3105 | 7467 | 1734 | 3375 |
| $AUC_{60}$/ng min ml$^{-1}$ | 474 | 764 | 3278 | 278 | 477 |
| $AUC_{30}$/ng min ml$^{-1}$ | 236 | 372 | 1999 | 97 | 172 |

TABLE I-continued

|  | 10 mg Invention | 20 mg Invention | 6 mg Sub-Cut | 10 mg Imitrex | 20 mg Imitrex |
|---|---|---|---|---|---|
| $AUC_{20}$/ng min ml$^{-1}$ | 136 | 215 | 1372 | 48 | 93 |
| BA/% | 17.2 | 12.5 | 100 | 13.9 | 13.6 |

As can be seen, the nasal administration of the present invention shows a significantly greater peak plasma concentration $C_{max}$ as compared with the existing Imitrex® nasal administration system having the same nominal amount of succinate base, and the concentration at twenty minutes $C_{20}$ is more than twice the concentration achieved by the existing Imitrex® nasal administration system.

In fact, the nasal administration system of the present invention has been established, by gamma-scintigraphic studies (in vivo and in vitro), to emit approximately 70% of the dose as contained in the capsule C, and even with an overage of 5% which is present in the capsule C, the actual amount of succinate base which is delivered by the nasal administration system of the present invention is about 8 mg for a 10 mg nominal and 16 mg for a 20 mg nominal. Thus, even more markedly improved results are predicted as compared with the existing Imitrex® nasal administration system on a dose-for-dose basis.

In addition, the nasal administration of the present invention shows a markedly shorter time maximum plasma concentration $T_{max}$ as compared to the existing Imitrex® nasal administration system having the same nominal amount of succinate base. In the present invention, the time maximum plasma concentration $T_{max}$ is about 20 minutes, which is about 70 minutes faster than that achieved with the conventional Imitrex® nasal administration system, and is approaching that of sub-cut delivery.

This markedly increased time maximum plasma concentration $T_{max}$ lends the present invention to indications where a rapid onset of action is required. In the present Example, this event is migraine, but the present invention can be utilized to treat pain in general, including other headaches, such as cluster headaches, and neuropathic pain, to induce sedation, to ameliorate or abort another CNS event, to abort a partial or full epilepsy seizure, to treat a panic disorder, to treat insomnia, to treat jet-lag, to regulate blood glucose levels, to influence satiety or the sense of satiety, or to deliver a memory-enhancing agent prior to a learning episode.

Further, in the nasal administration of the present invention, the area under the curve to 30 minutes ($AUC_{30}$) is greater than twice that achieved with the conventional Imitrex® nasal administration system and approaching 2.5 times greater for the 10 mg nominal dose.

Still further, in the nasal administration of the present invention, the area under the curve to 20 minutes ($AUC_{20}$) is greater than twice that achieved with the conventional Imitrex® nasal administration system and approaching three times greater for the 10 mg nominal dose.

In addition, with the nasal administration of the present invention, the time course for the measured blood plasma concentration following administration shows a bifurcated trace, which has two peaks and is indicative of a hybrid absorption mechanism, with the early absorption being nasal absorption and the later, delayed absorption being oral or GI absorption. Studies have shown that oral absorption is very limited within a period of 20 minutes following administration, and thus it can be assumed that the absorption in the period to 20 minutes following administration relates essentially only to nasal absorption.

On this basis, the bi-directional administration of the present invention provides a significantly greater ratio of nasal absorption fraction to total bioavailability (BA), which clearly demonstrates the improved pharmacokinetics of the present invention. The present invention achieves a ratio of about 2.21, which compares with a ratio of about 0.71 for the conventional Imitrex® nasal administration system, where the nasal absorption fraction of the total BA is about 10% (Fuseau, E et al, Clinical Pharmacokinetics of Intranasal Sumatriptan, Drug Deposition, 41(11), 2002, pages 801 to 811) and the total BA after nasal administration is about 14%.

From data available for other triptans delivered both as a nasal spray and orally (Goadsby, P, Zolmitriptan Intranasal: A Review of the Pharmacokinetics and Clinical Efficacy, Headache, 2006, 46, pages 138 to 149), zolmitriptan has a ratio of about 0.75, where the fraction of nasal absorption is about 30% and the total BA is about 40%. In this study, the fraction absorbed nasally was calculated by preventing absorption via the GI tract through the use of charcoal.

The markedly-improved pharmacokinetics of the nasal administration of the present invention is clearly shown in FIG. 3, which shows the time course for the averaged measured blood plasma concentration following administration of the sumatriptan succinate powder (10 mg sumatriptan base) by the bi-directional nasal administration of the present invention as compared to the corresponding historic averaged measured blood plasma concentration following intranasal administration of the 10 mg sumatriptan base Imitrex® nasal spray administration system.

The efficacy of the present invention is particularly surprising as the formulation of the present invention includes no absorption enhancer or muco-adhesive.

In the EEG analysis, the EEG profiles for the subjects when treated with the 10 mg and 20 mg intranasal administration of the present invention were broadly similar to the 6 mg sub-cut administration.

Previously, Thomaides, T et al, EEG and topographic frequency analysis in migraine attack before and after sumatriptan infusion, Headache, 36, pages 111 to 114, 1996, have determined that the main effects on the EEG associated with GTN-induced headaches are significant increases in relative values for the delta and theta frequency bands, with decreases in the alpha and beta frequency bands not reaching significance.

The treatment effects on the EEG relative energy parameter for each recording time are summarized in Table II hereinbelow for each frequency band (FB). A significant ($p<0.05$ for sufficiently large number of scalp electrodes) IMP drug to comparator increase is indicated by a closed arrow, and a significant IMP drug to comparator decrease is indicated by an open arrow. An arrow between brackets indicates a statistical trend (4-5 electrodes display $p<0.05$).

TABLE II

| Sumatriptan Intranasal | 10 mg Invention | | | | 20 mg Invention | | | |
|---|---|---|---|---|---|---|---|---|
| FB time (min) | Δ | θ | α | β | Δ | θ | α | β |
| First 10 | (↑) | | (⇓) | | ↑ | | ⇓ | |
| 20 | | ↑ | ⇓ | | | (↑) | ⇓ | |
| 30 | | ↑ | | | | | | |

TABLE II-continued

| Sumatriptan Intranasal | 10 mg Invention | | | | 20 mg Invention | | | |
|---|---|---|---|---|---|---|---|---|
| FB time (min) | Δ | θ | α | β | Δ | θ | α | β |
| 40 | | | | | | | | ⇓ |
| 50 | | | | | | | | |
| 60 | | | | | | | | |
| 70 | | | | ⇓ | | | | |
| 80 | | | | | | | | |
| 90 | | | | | | | | |
| 2 h | | | | | | | | ⇓ |
| 4 h | | | | | | | | |
| 6 h | | | | | | | | |
| 8 h | | | | | | | | ⇓ |

As regards the theta relative energy, increases in theta relative energy were observed, as compared with the 6 mg sub-cut comparator administration. The largest differences with active comparator, which occurred over almost the entire right half and left posterior scalp from 20 to 40 minutes, were observed for the 10 mg administration, and these differences were less pronounced for the 20 mg administration.

As regards the delta relative energy, increases in the delta relative energy were more transient in the first 10 minutes for the 10 mg and 20 mg administrations, but more pronounced for the 20 mg administration.

As regards the alpha relative energy, both the 10 mg and 20 mg administrations decreased the alpha relative energy for a duration of 20 minutes over large portions of the anterior scalp, and additionally over the period from 30 to 40 minutes for the 20 mg administration.

Only few unsystematic modifications were observed in the absolute frequency band energies. For the additional parameters, it is worthwhile to note that the ASI, a measure of cortical arousal, was decreased for both the 10 mg and 20 mg administrations over large portions of the anterior scalp and displayed between 10 and 40 minutes, in addition spreading over posterior scalp regions for the 20 mg administration.

FIG. 4 illustrates median maps for theta and alpha relative energies for the 10 mg and 20 mg nasal administrations of the present invention and the 6 mg comparator sub-cut administration.

As illustrated, in the present study, the most salient effects of the 6 mg sub-cut administration were in sustained reductions from 0 to 40 minutes in theta activity (row 3), mostly in relative spectral contributions, and this was accompanied for a period of about half an hour by increased relative beta contributions. In addition, there were some signs of decreased delta activity (absolute and relative) but little effects in alpha activity emerged, but noting the trends for occipital increases (row 6). Overall, the best EEG-markers reflecting the restoring potential of sumatriptan are the relative energy values.

In the present study, pre-treatment with the 6 mg sub-cut administration completely prevented the excess in theta induced by sublingual GTN and resulted in depressed theta for 40 minutes. This is in agreement with studies by others. Indeed, in subjects in which an excess by more than 15% of theta (delta only a few percent) had been induced by the GTN challenge, this effect was reversed within 30 minutes after treatment with sumatriptan pharmacotherapy. And, when given via the intranasal route of administration, the 10 mg and 20 mg nasal administrations of sumatriptan powder induced, coarsely speaking, a similar EEG profile as the sub-cut comparator.

The fact that the nasal administrations of the present invention provide a similar EEG profile as the sub-cut comparator is particularly surprising given the very large differences in the $C_{max}$ values for the nasal administrations of the present invention (10.5 and 15.9) as compared to the sub-cut comparator (87.4). The reason for this surprising result is not known, but the present inventors speculate that there could be a number of reasons.

Firstly, it is known that the rate of abruption is apparently more important than the extent of absorption (Fox, W, Onset of Effect of 5-HT1B/1D Agonists: A Model with Pharmacokinetic Validation, Headache, 44, 2004, pages 142 to 147), and the rate of absorption of the sumatriptan powder of the present invention is similar to the sub-cut comparator and much faster than that of the conventional Imitrex® nasal administration system.

Another possible reason is a direct nose-to-brain absorption mechanism, which has been shown in animal studies. A further possible reason is absorption through "counter current" transport via the sinus cavernous and the carotid artery, and, whilst sumatriptan passes the BBB poorly, sumatriptan is able to pass the BBB to some extent. A still further possible reason is direct or indirect action via the trigeminal and olfactory nerves, which is involved in the pathogenesis of migraine.

EXAMPLE #2

This study provides for characterization of the deposition as achieved by the nasal administration system of the present invention as used in the above-described study.

In this study, eight healthy subjects were studied.

In separate sessions, the subjects each received a test powder formulation, comprising radio-labelled lactose, using the nasal administration system of the present invention.

The lactose powder, as supplied by Friesland Foods Domo (Zwolle, The Netherlands), had a nominal mean particle size of 15 μm, with 10% having a particle size of less than 3 μm, 50% having a particle size less than 15 μm and 90% having a particle size less than 38 μm.

The lactose powder was "hot" radio-labelled with technetium 99Tc, using the labelling procedure disclosed in Karhu, M et al, International Journal of Pharmaceutics, 196, 2000, pages 95 to 103 (2.1—Labelling of lactose particles). In this procedure, the lactose powder was dispensed in a lead box with a HEPA-filtered air stream and using an aseptic technique.

The deposition of the test powder in the nasal cavity was imaged using a scintillation camera system, here a VERTEX camera as supplied by ADAC Laboratories (USA) which was equipped with a low energy parallel hole high resolution VXGP collimator.

The powder was administered with the subjects sitting in the upright position, and, following administration, the subjects sat back such that the floor of the nasal cavity was projected at between 30 and 45 degrees with respect to the y-axis of the camera detector. This re-positioning took approximately 1 minute from the dose administration and imaging was initiated immediately thereafter. A total of 16 images, each containing 128×128 pixels, were acquired at two minute intervals. The subjects were instructed not to sniff during the imaging procedure.

As a consequence of the variation in administered activity, the acquired images were normalized so that the first image in each series, which represents the initial deposition, had a total image intensity equal to 100,000 within a region drawn around the nose as appearing in the cumulative images. As the floor of the nose and the curvature of the pharynx were clearly visible in the cumulative images as derived from each of the series, each series of images could conveniently be aligned.

Nasal dimensions were measured by acoustic rhinometry using Rhin2000 anatomic nose adaptors as supplied by RhinoMetrics (Lynge, Denmark), to verify normal nasal dimensions and to assist in nasal segmentation.

Acoustic rhinometry identified the location of the minimal cross-sectional area corresponding to the head of the inferior turbinate, the head of the middle turbinate and the transition to the epipharynx.

Figure 1A:
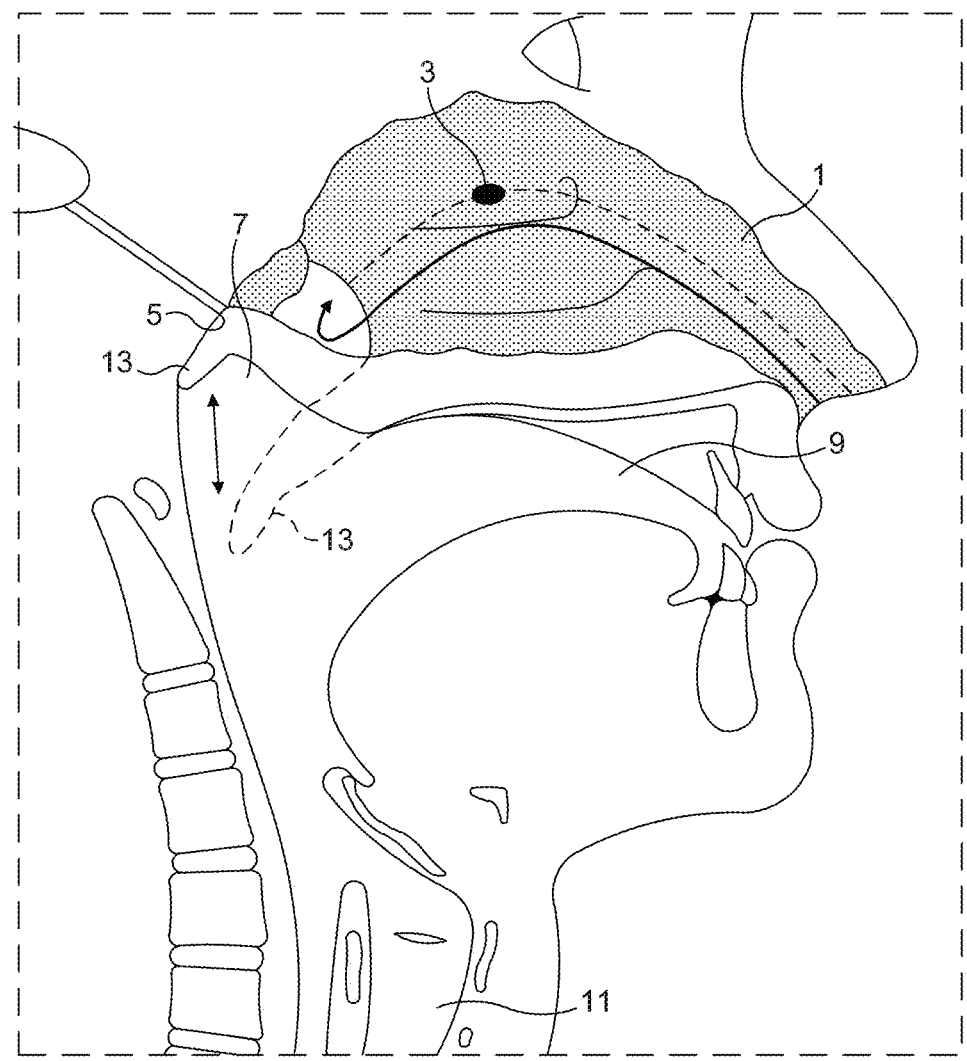
FIG. 1(b) illustrates the segmentation of a nasal cavity in accordance with a preferred embodiment of the present invention.
Figure 1B:
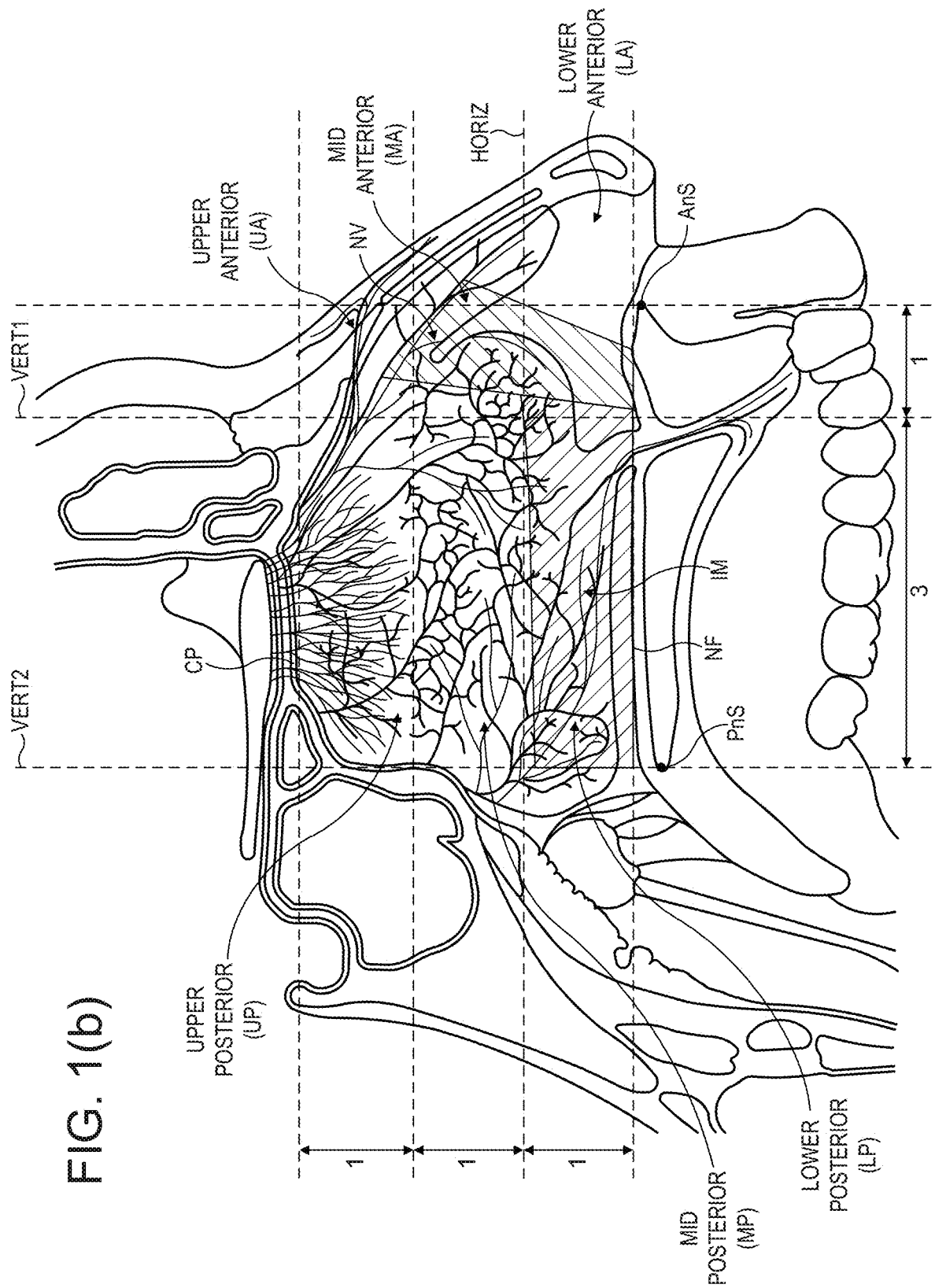

In order to allow for characterization of the deposition, the nose region was segmented into six rectangular nasal regions, as illustrated in FIG. 1(b), namely, a lower anterior region (LA), a mid anterior region (MA), an upper anterior region (UA), a lower posterior region (LP), a mid posterior region (MP) and an upper posterior region (UP), and one pharyngeal region.

The vertical segmentation VERT1 which defines the anterior and posterior segments is at a point just posterior to the anterior limitation of the inferior turbinate, and the vertical segmentation VERT2, which defines the posterior nasal segment and the nasopharynx is at the posterior margin of the inferior turbinate. In this embodiment, for the purposes of the detection analysis, the anterior bound of the anterior segment was set at 15 pixels anterior to the vertical segmentation VERT1 and the posterior bound of the nasopharynx region was set at 15 pixels posterior to the vertical segmentation VERT2.

The horizontal segmentation HORIZ1, HORIZ2 which define the lower, mid and upper vertical segments are at heights of one-thirds and two-thirds of the distance between the lower and upper boundaries of the nasal cavity as defined by the nasal floor and the cribiform plate. In this embodiment the nasal floor was determined to be about 4 mm (c2 pixels) above a radio-labelled marker at the palette in the oral cavity, and the height of the nasal cavity was determined from the location of the olfactory bulb, which was determined to be between 38 and 45 mm (c18-21 pixels) depending upon the subject.

Table III below shows the mean values for the initial deposition in the six nasal segments and the nasopharynx, as represented by the first in the series of images for each of the subjects.

TABLE III

| Image | Percentage (%) |
|---|---|
| Upper Anterior (UA) | 1.7 |
| Mid Anterior (MA) | 10.7 |
| Lower Anterior (LA) | 5.9 |
| Upper Posterior (UP) | 17.4 |
| Mid Posterior (MP) | 41.4 |
| Lower Posterior (LP) | 20.9 |
| Nasopharynx (NP) | 2.0 |

As can be seen, the bi-directional administration system provides for initial deposition of greater than 80% beyond the nasal valve of the total dose as deposited in the nasal cavity, and greater than 57% of the total dose as deposited in the nasal cavity is deposited in the upper posterior two thirds of the nasal cavity. This deposition pattern contrasts markedly with existing nasal delivery devices, where between 50 and 80% of the delivered dose is deposited anterior of the nasal valve.

The present inventors attribute this deposition pattern as an important contributing factor to the surprisingly enhanced efficacy as achieved in the study of Example #1. As mentioned hereinabove, the present inventors postulate that deposition in the upper posterior region, and in particular the upper posterior two thirds, which has a single-cell mucosal layer, allows for a direct nose-to-brain absorption mechanism, absorption through "counter current" transport via the sinus cavernous and the carotid artery, and direct or indirect action via the olfactory and trigeminal nerves, which is involved in the pathogenesis of migraine.

Finally, it will be understood that the present invention has been described in its preferred embodiments and can be modified in many different ways without departing from the scope of the invention as defined by the appended claims.

The present invention has been exemplified in relation to sumatriptan, but it will be understood that the present invention has application to many other substances, including other triptans, such as risatriptan, naratriptan, eletriptan, frovatriptan and zolmitriptan, and other analgesics, such as ergotamines, including dihydroergotamine mesylate, ergonovine maleate and ergotamine tartrate with caffeine, fentanyl, oxycondone, hydromorphone, morphine, codeine, ketobbemidone, cocaine and opiods in general.

The present invention also has application to benzodiazepines, such as midazolam.

The present invention further has application in relation to non-steroidal anti-inflammatory drugs (NSAIDs), for example, aspirin, ibuprofen, naproxen, indomethacin, diclofenac and ketoprofen.

The present invention still further has application in relation to proteins and peptides, in particular having a molecular weight greater than 1000 g/mol, which typically have a very low oral bio-availability, often less than 1%.

Particular examples include insulin, including its analogues and derivatives, desmopressin and calcitonin.

The present invention yet still further has application in relation to powder vaccines, immunomodulators and immunostimulators.

In summary, the present invention has application in relation to the following broad definitions of molecules.

(I) Small molecules (<1000) with relatively fast nasal absorption and high nasal BA, such as fentanyl, midazolam and oxycodone. The present invention suggests far more rapid CNS effects than compared to the prior art nasal administration systems, which could be because of differences between arterial and venous concentrations, where arterial absorption is between about 25% and 50% greater than venous absorption, possible "counter current" transport to the sinus cavernous and the carotid artery, which must pass the BBB, which has been shown to be about 25% greater in animal studies, and possible direct N2B transport along the olfactory and trigeminal nerves (Einer-Jensen, N et al, Pharmacol. Toxicol., 87(6), 2000, pages 276 to 278, Einer-Jensen, N et al, Exp. Brain Res., 130(2), 2000, pages 216 to 220, and Dale, O et al, Intranasal Midazolam: a comparison of two delivery devices in human volunteers, J. Pharmacy and Pharmacology, 58, 2006, pages 1311 to 1318). N2B transport and clinical effects via the trigeminal nerves are not, however, necessarily reflected in the traditional PK profile.

(II) Small and medium sized molecules with relatively poor BA, such as sumatriptan and zolmitriptan. For the sumatriptan powder of the present invention, sumatriptan passes the BBB relatively poorly, but animal studies suggest that sumatriptan can be transported directly to the brain by direct N2B mechanisms (Gladstone, J P, Newer formulations of triptans: Advances in migraine treatment, Drugs, 63, 2003, pages 2285 to 2305). The present invention provides for increased absorption, which is particularly relevant where rapid absorption and a fast onset of action are desirable. The present invention suggests more rapid CNS effects, which could be because of possible direct N2B uptake, possible "counter current" transport to the sinus cavernous and the carotid artery, where the molecule is able to pass the BBB, and possible direct N2B transport along the olfactory and trigeminal nerves.

(III) Larger molecules (>1000), including peptides and proteins, which have low nasal BA, typically between about 3 and 15%, and very poor oral BA, typically less than 1%, because of degradation in the GI tract. The present invention, in providing a powder formulation, is particularly suited to the delivery of peptides and proteins, where the powder can provide for improved nasal absorption, but also can have improved stability. For these substances, it is postulated that there may be a dedicated transport mechanism along the olfactory and trigeminal nerves directly to the cerebral structures, which is not via the CSF. As such, measurements from the CSF may not show the presence of active substance, but a substantial effect may be present in the brain and exert clinical effects, as exemplified in a recent study (Thorne, R G et al, Delivery of insulin-like growth factor-I to the rat brain and spinal cord along olfactory and trigeminal pathways following intranasal administration, Neuroscience, 127(2), 2004, pages 481 to 496).

The invention claimed is:

1. A device for delivering a powdered sumatriptan substance to a nasal cavity of a subject, comprising:
   a nosepiece configured to be fitted to a nostril of the subject, wherein the nosepiece is configured to extend into the nostril of the subject and expand at least a portion of a nasal valve of the subject; and
   a substance containing unit connected to the nosepiece, the substance containing unit containing the powdered sumatriptan substance to be delivered to the nasal cavity of the subject, the powdered sumatriptan substance comprising a particle size distribution in which at least 10% of the particles are less than about 20 µm, at least 50% of the particles are less than about 50 µm, at least 50% of the particles are greater than about 30 µm, and at least 90% of the particles are less than about 150 µm; and
   a trap disposed between the substance containing unit and the nosepiece;
   wherein the device is configured such that, when the nosepiece is fitted to the nostril of the subject, oral exhalation by the subject through the substance containing unit and the nosepiece acts to close the oropharyngeal velum of the subject and produce an exhalation flow passing into one nasal passage of the subject and out of the other nasal passage of the subject, thereby achieving a bi-directional exhalation flow for delivering the powdered sumatriptan substance to a portion of the nasal cavity of the subject.

2. The device of claim 1, wherein the powdered sumatriptan substance comprises a sumatriptan base or sumatriptan succinate.

3. The device of claim 1, wherein the powdered sumatriptan substance contains only sumatriptan succinate and no introduced excipients or adjuvants.

4. The device of claim 1, wherein the powdered sumatriptan substance to be delivered to the nasal cavity of the subject is disposed in a substance container.

5. The device of claim 4, wherein the substance container is a capsule.

6. The device of claim 4, wherein the substance container contains a 10 mg dose of the powdered sumatriptan substance.

7. The device of claim 1, wherein the powdered sumatriptan substance to be delivered to the nasal cavity of the subject is disposed in a capsule.

8. The device of claim 1, wherein the powdered sumatriptan substance has a particle size distribution in which at least 10% of the particles are less than about 10 μm and at least 90% of the particles are less than about 90 μm.

9. A device for delivering powdered sumatriptan substance to a nasal cavity of a subject, comprising:

- a mouthpiece configured to be fitted to an oral cavity of the subject;
- a nosepiece configured to be fitted to a nostril of the subject, wherein the nosepiece is configured to extend into the nostril of the subject and expand at least a portion of a nasal valve of the subject;
- a substance containing unit connected to the nosepiece, the substance containing unit containing the powdered sumatriptan substance to be delivered to the nasal cavity of the subject, the powdered sumatriptan substance comprising a particle size distribution in which at least 10% of the particles are less than about 20 μm, at least 50% of the particles are less than about 50 μm, at least 50% of the particles are greater than about 30 μm, and at least 90% of the particles are less than about 150 μm; and
- a trap disposed between the substance containing unit and the nosepiece;
- wherein the device is configured such that, when the nosepiece is fitted to the nostril of the subject and the mouthpiece is fitted to the oral cavity of the subject, oral exhalation by the subject through the mouthpiece, through the substance containing unit, and through the nosepiece acts to close the oropharyngeal velum of the subject and produce an exhalation flow passing into one nasal passage of the subject and out of the other nasal passage of the subject, thereby achieving a bi-directional exhalation flow for delivering the powdered sumatriptan substance to a portion of the nasal cavity of the subject.

10. The device of claim 9, wherein the powdered sumatriptan substance comprises a sumatriptan base or sumatriptan succinate.

11. The device of claim 9, wherein the powdered sumatriptan substance contains only sumatriptan succinate and no introduced excipients or adjuvants.

12. The device of claim 9, wherein the powdered sumatriptan substance to be delivered to the nasal cavity of the subject is disposed in a substance container.

13. The device of claim 12, wherein the substance container is a capsule.

14. The device of claim 12, wherein the substance container contains a 10 mg dose of the powdered sumatriptan substance.

15. The device of claim 9, wherein the powdered sumatriptan substance to be delivered to the nasal cavity of the subject is disposed in a capsule.

16. The device of claim 9, wherein the powdered sumatriptan substance has a particle size distribution in which at least 10% of the particles are less than about 10 μm and at least 90% of the particles are less than about 90 μm.

17. The device of claim 9, further including a labyrinthine structure disposed between the mouthpiece and the substance containing unit.

\* \* \* \* \*